United States Patent [19]

Westlake

[11] Patent Number: 5,048,683
[45] Date of Patent: Sep. 17, 1991

[54] SPONGE COUNTER BAG

[75] Inventor: Betsy Westlake, Norton, Mass.

[73] Assignee: The Kendall Company, Mansfield, Mass.

[21] Appl. No.: 521,494

[22] Filed: May 10, 1990

[51] Int. Cl.$^5$ .............................................. B65D 30/22
[52] U.S. Cl. .................................... 206/362; 206/370; 206/438; 383/39
[58] Field of Search ............... 206/362, 363, 370, 438; 383/38, 39

[56] References Cited

U.S. PATENT DOCUMENTS

| | | | |
|---|---|---|---|
| 3,749,237 | 7/1973 | Dorton | 206/438 |
| 4,234,086 | 11/1980 | Dorton | 206/362 |
| 4,361,231 | 11/1982 | Patience | 383/39 |
| 4,422,548 | 12/1983 | Cheesman et al. | 206/370 |
| 4,765,472 | 8/1988 | Dent | 383/39 |
| 4,884,360 | 12/1989 | Pearcy | 383/39 |
| 4,887,715 | 12/1989 | Spahn et al. | 206/370 |

FOREIGN PATENT DOCUMENTS 8902726  4/1989  PCT Int'l Appl. ................ 206/370

Primary Examiner—Jimmy G. Foster
Attorney, Agent, or Firm—Alvin Isaacs

[57] ABSTRACT

A sponge counter bag comprising, a backing sheet of flexible material having a front surface, a rear surface, a pair of side edges, and a pair of end edges connecting the side edges. The bag has a plurality of pockets progressively disposed on the front surface of the backing sheet intermediate said end edges, with the pockets comprising a flap of flexible material having a pair of side edges, a lower edge joined to the backing sheet, and an upper edge extending between said side edges, with the upper edge of the flap defining an opening intermediate the flap and backing sheet to receive sponges. The side portions of the flap adjacent its side edges are joined to the backing sheet adjacent the side edges of the backing sheet, and a lower portion of the flap is joined to the backing sheet along a line intermediate the side portions of the flap, with the joinder line having a raised lateral center portion and defining at least one opening to permit passage of fluid through the opening to a lower portion of the flap and capture the fluid beneath the joinder line.

11 Claims, 1 Drawing Sheet

SPONGE COUNTER BAG

BACKGROUND OF THE INVENTION

The present invention relates to counter bags for surgical sponges.

During surgical procedures, absorbent sponges are utilized to absorb body fluids around the site of surgical incision. The sponges are normally provided in two sizes, e.g., a smaller size sponge on the order of about 4 inch×4 inch and a larger size on the order of 18 inch×18 inch. In the past, when the wetted sponges are removed from the patient's body, they have been placed in a kick bucket for retention during the surgical procedure. At the end of the surgical procedure, the sponges are removed from the kick bucket and were sorted according to size, after which they were counted to assure that no sponges were left in the patient's body. According to convention, the 4 inch×4 inch sponges were counted in groups of ten, and the 18 inch×18 inch sponges were counted in groups of five.

It will be apparent that the prior sorting and counting procedure was tedious and time consuming, and could be subject to error during the counting of sponges. A back strip has been proposed in U.S. Pat. No. 3,749,237 in an attempt to facilitate this procedure. This back strip has a spot heat seal which divides the pocket into two compartments to be used for small surgical sponges, and the spot can be broken open to use the entire pocket for one large laparotomy sponge. An alternate design is disclosed in U.S. Pat. No. 4,361,231 in which a heat seal line extends from a lower edge of each pocket toward the center to divide the pocket for two small surgical sponges, and an entire pocket can be used for one large surgical sponge.

The prior bag designs do not contain the fluid which drains off the sponges when the bag is removed from its stand for disposal. Typically, the bag is removed by folding the bag up from the bottom, containing the sponges and fluid together. The bag is then removed from a support stand and it is discarded with the sponges remaining in the pockets or pouches. During this time, there is a tendency for some of the fluid from the sponges to escape out of the bag during disposal resulting in possible spilling of fluid from the bag and possible contamination. In addition, when the spot seal in the previous bags were broken, holes remained in the bag where the seal was broken permitting a location for fluid to leak out of the pockets during disposal.

SUMMARY OF THE INVENTION

A principal feature of the present invention is the provision of an improved sponge counter bag.

The sponge counter bag of the present invention comprises, a backing sheet of flexible material having a front surface, a rear surface, a pair side edges, and a pair of end edges connecting the side edges. The bag has a plurality of pockets progressively disposed on the front surface of the backing sheet intermediate the end edges, with the pockets comprising a flap of flexible material having a pair of side edges, a lower edge joined to the backing sheet, and an upper edge extending between the side edges, with the upper edge of the flap defining an opening intermediate the flap and backing sheet to receive sponges. The side portions of the flap adjacent its side edges are joined to the backing sheet adjacent the side edges of the backing sheet, with the lower portion of the flap being joined to the backing sheet along a line intermediate the side portions of the flap, with the joinder line having a raised lateral central portion and defining at least one opening.

A feature of the present invention is that fluid is permitted to pass through the opening to a lower part of the pockets for retention therein.

Yet another feature of the invention is that the joinder line captures the fluid in the lower part of the pocket.

Another feature of the invention is that the joinder line prevents passage of fluid toward the upper opening during disposal of the bag.

Still another feature of the invention is that the joinder line eliminates the necessity of spot seals to separate the pockets of the bag.

A further feature of the invention is that the counter bag of the present invention reduces the possibility of contamination.

Still another feature of the invention is that the bag counter of the present invention minimizes the possibility of fluid spilling out of the pockets during disposal.

Yet another feature of the invention is that the counter bags may be constructed in a simplified manner.

A further feature of the invention is that the bag collects either small or larger sponges in the pockets.

Further features will become more fully apparent in the following description of the embodiments of this invention and from the appended claims.

DESCRIPTION OF THE PREFERRED EMBODIMENTS

Figure 1:
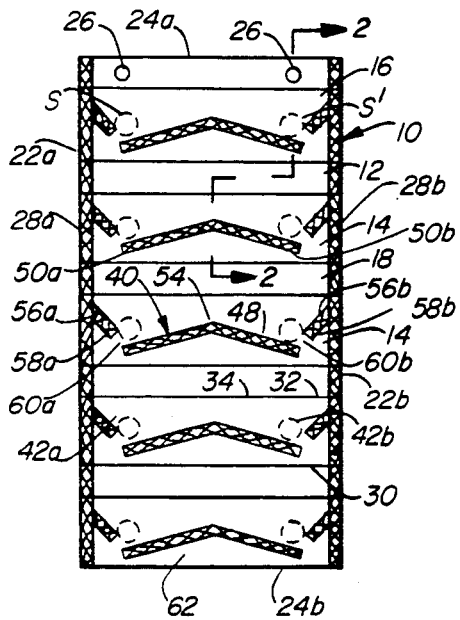
FIG. 1 is a front plan view of a sponge collection bag of the present invention showing the bag as used for collecting smaller sponges.
Figure 2:
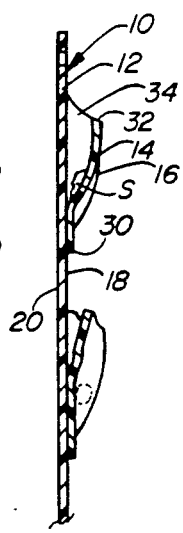
FIG. 2 is a fragmentary sectional view taken substantially as indicated along the line 2—2 of FIG. 1.

Referring now to FIGS. 1 and 2, there is shown a sponge collection or counter bag generally designated 10 comprising a backing sheet 12 of flexible material having a plurality of pockets 14 each comprising a flap 16 of flexible material joined to the backing sheet 12. The backing sheet 12 and flap 16 may be constructed from any suitable plastic material, such as polyethelene. The backing sheet 12 is of generally rectangular shape, and has a front surface 18, a rear surface 20, a pair of opposed side edges 22a and 22b, and a pair of opposed end edges 24a and 24b connecting the side edges 22a and b. The backing sheet may have a pair of spaced openings 26 located adjacent the end edge 24a for suspending the device 10 from a suitable instrument received through the openings 26.

The flap 16 has a pair of opposed side edges 28a and 28b, a lower edge 30 extending between the side edges 28a and b, and an upper edge 32 extending between the side edges 28a and b. As shown, the side edges 28a and b of the flap 16 are joined to the front surface 18 of the backing sheet 12 adjacent the side edges 22a and b of the backing sheet 12 by suitable means, such as by heat sealing. The upper edges 32 of the flaps 16 define associated openings 34 intermediate the flap 16 and backing sheet 12 to receive soiled sponges in the pockets 14. Also, the pockets 14 are progressively disposed along the backing sheet 12 between the end edges 24a and b, with the upper edges 32 of lower flaps 16 being located adjacent the lower edges 30 of adjacent upper flaps 16. In a preferred form, the device has five pockets 14 disposed along the backing sheet 12 for a purpose which will be described below.

Figure 3:
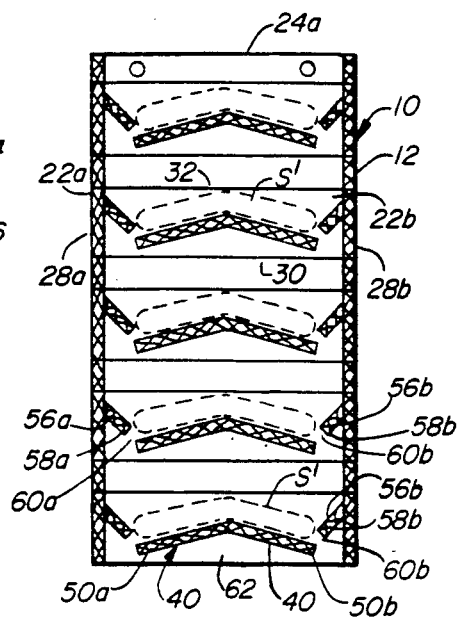
FIG. 3 is a front plan view of the sponge collection bag showing the bag as used for collecting larger sponges.

As shown in FIGS. 1-3, lower portions 46 of the flaps 16 are joined to the backing sheet 12 along a joinder line generally designated 40 having a first line 48 extending between opposed lower parts of the flaps 16 toward a raised lateral central portion of the flap 16 and joinder line 40, with the first line 48 having a lateral central apex 54 which separates the pockets 14 into a pair of compartments 42a and 42b to receive a pair of smaller sponges at locations in the compartments on opposed sides of the apex 54. Alternately, as shown in FIG. 3, one larger sponge may be placed in each of the pockets 14, with each larger sponge extending over the apex 54 and along sides of the first line 48 on opposed sides of the apex 54. As shown, lower opposed ends 50a and b of the first line 48 of the joinder line 40 are spaced from the side edges 28a and b of the flap 16 and the lower edge 30 of the flaps 16. The joinder line 40 has a pair of opposed second lines 56a and 56b extending downwardly from the opposed side edges 28a and b of the flap 16 toward the first line 48 and having ends 58a and 58b spaced from the first line 48 to define a pair of opposed openings or apertures 60a and 60b intermediate the first line 48 and second lines 56a and 56b, respectively. As shown, the ends 58a and b of the second lines 56a and b, respectively, are located intermediate the ends 50a and b of the first line 48 and the apex 54 of the first line 48.

In accordance with the present invention, during use of the bag 10, fluid from the sponges drain through the aperture 60a and b to a cavity 62 beneath the first and second lines 48 and 56a and b, where the fluid is retained in the lower part of the pockets 14 during use. Thus, the fluid is conveniently stored in the bag 10 during drainage from the sponges. During disposal of the bags 10, the bags are folded upwardly for disposal, and the fluid is captured in the cavities 62 at the lower part of the pockets 14 due to the configurations of the first lines 48 and second lines 56a and b in order to prevent passage of fluid out of the pockets 14 during disposal. In this manner, the bag 10 of the present invention prevents spilling of fluid out of the bags during disposal. In addition, the bags 10 of the present invention eliminates the rupturing of holes or openings in the flaps 16, and thus prevent possible passage of fluid through such nonexistent openings.

In use, with reference to FIGS. 1 and 2, the backing sheet 12 is suspended from a suitable instrument passing through the openings 26 of the backing sheet 12. During a surgical procedure, small soiled sponges S may be placed in the pockets 14 with each smaller sponges S being located in one of the compartments 42a and b of the pockets 14. Thus, during collection of smaller sponges S by the device 10 two smaller sponges S are placed in each pocket 14 on opposed sides of the flaps 16. Since five pockets 14 are located on each backing sheet 12, a total of ten smaller sponges S may be collected in each of the devices 10 during the placement procedure. Thus, the device 10 serves to collect soiled sponges in pockets 14 and automatically counts a total of ten smaller sponges in each of the devices 10. However, with reference to FIG. 3, when larger soiled sponges $S^1$ are removed from the patient's body, one larger sponge $S^1$ may be placed in each of the pockets 14, with opposed ends of the larger sponges $S^1$ being located in the opposed compartments 42a and b of each pocket 14. Thus, the device 10 may be utilized to collect larger sponges $S^1$, and since there are five pockets 14 located in each device 10, the device 10 collects and automatically counts five larger sponges $S^1$ in the pockets 14 of each device 10. Accordingly, the joinder line 40 divides the pockets 14 into the compartments to permit selective placement of two smaller sponges S in each compartment in each pocket 14, or a larger sponge $S^1$ in each pocket 14. Thus, the soiled sponges may be separated into smaller or larger sponges during the collection and counting procedure in each of the devices 10. As previously discussed, the fluid draining from the sponges S or $S^1$ during the counting procedure is captured in a lower part of the pockets 14 of the bag 10, and is retained in the lower part of the pockets 14 during disposal of the bags 10 after use to prevent possible passage of fluid from the pockets 14 and contamination which may result from such spillage of fluid.

Figure 4:
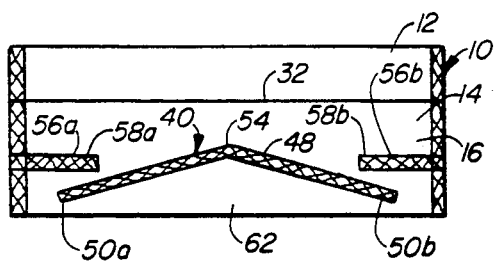
FIG. 4 is a front plan view of another embodiment of a pocket for the bag of the present invention.

Another embodiment of the present invention is illustrated in FIG. 4, in which like reference numerals designate like parts. In this embodiment, the second lines 56a and b extend laterally from the opposed side edges 28a and b of the flaps 16 toward the first line 48, with the inner ends 58a and b of the second lines 56a and b being located above the lower ends 50a and b of the first line 48, and with the apertures 60a and b being located intermediate the ends 58a and b of the second lines 56a and b can the first line 48. In other respects, the bag of FIG. 4 operates in the same manner as the bag previously discussed in connection with FIGS. 1-3.

Figure 5:
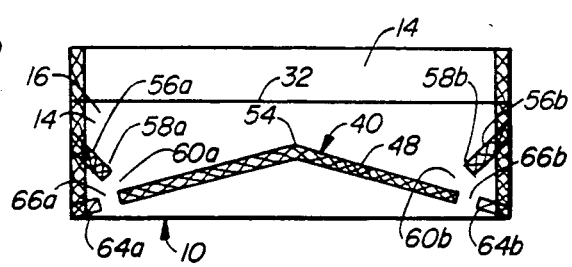
FIG. 5 is a front plan view of another embodiment of the pocket for the bag of the present invention.

Another embodiment of the present invention is illustrated in FIG. 5, in which like reference numerals designate like parts. In this embodiment, the lower ends 50a and b of the second lines 56a and b are located adjacent the lower ends 58a and b of the first line 48, respectively, with the apertures 60a and b being located adjacent the lower ends 50a and b of the first line 48. In this embodiment, the joinder line 40 has a pair of opposed third lines 64a and 64b extending from the opposed junctures of the side edges 28a and b of the flaps 16 and the lower edges 30 of the flaps 16 towards the lower ends 50a and b of the first line 48 to define a second pair of openings or apertures 66a and 66b intermediate the third lines 64a and b and the first line 48. In other respects, the bag 10 of FIG. 5 operates in the manner as previously discussed in connection with the bag 10 of FIGS. 1-3.

Figure 6:
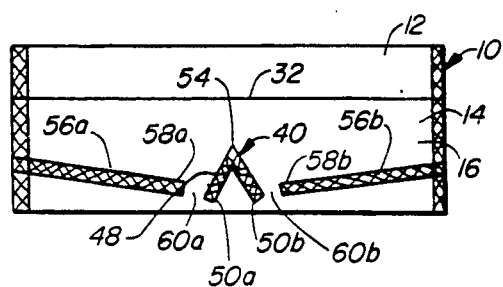
FIG. 6 is a front plan view of another embodiment of the pocket for the bag of the present invention.

Another embodiment of the counter bag 10 of the present invention is illustrated in FIG. 6, in which like reference numerals designate like parts. In this embodiment, the pockets 14 of the bag 10 are similar to that discussed in connection with FIGS. 1-3, with the exception that the lower ends 50a and b of the first line 48 and the inner ends 58a and b of the second lines 56a and b, respectively, are located adjacent the lateral central portion of the pockets 14, with the apertures 60a and b being located intermediate the ends 58a and b of the second lines 56a and b and the ends 50a and b of the first line 48. In other respects, the bag 10 of FIG. 6 is similar to that previously discussed in FIGS. 1-3.

Figure 7:
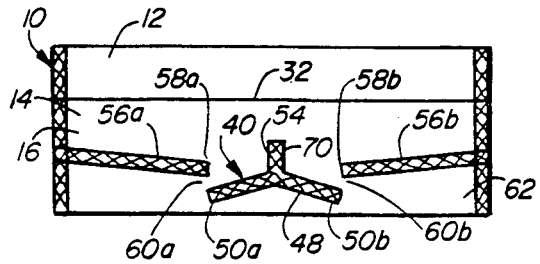
FIG. 7 is a front plan view of another embodiment of the pocket for the bag of the present invention.

Another embodiment of the bag of the present invention is illustrated in FIG. 7, in which like reference numerals designate like parts. In this embodiment, the lateral central portion of the joinder line 40 comprises a vertical line 70 which extends from downwardly tapered opposed legs of the first line 48. In other respects, the pocket 14 of FIG. 7 is similar to that previously discussed in connection with FIGS. 1-3.

The foregoing detailed description is given for clearness of understanding only, and no unnecessary limitations should be understood therefrom, as modifications will be obvious to those skilled in the art.

I claim:

1. A sponge counter bag, comprising:
   a backing sheet of flexible material having a front surface, a rear surface, a pair of side edges, and a pair of end edges connecting the side edges; and
   a plurality of pockets progressively disposed on the front surface of the backing sheet intermediate said end edges, said pockets comprising a flap of flexible material having a pair of side edges, a lower edge joined to the backing sheet, and an upper edge extending between said side edges, with the upper edge of the flaps defining an opening intermediate the flap and backing sheet to receive sponges, with a side portion of the flaps adjacent its side edges being joined to the backing sheet adjacent the side edges of the backing sheet, and with a lower portion of the flaps being joined to the backing sheet along with a first and a pair of second joinder lines, the first joinder line extending between and spaced from the opposed side edges of each of the flaps, the second joinder lines extending from the opposed side edges of each of the flaps toward the first joinder line and having ends spaced from the first joinder line to define a pair of opposed openings in each of said flaps to permit passage of fluid between the first and second joinder lines to a lower portion of the flaps, whereby to capture the fluid beneath the joinder lines.

2. The bag of claim 1 wherein the side portions of the flaps comprise the side edges of the flaps.

3. The bag of claim 1 wherein the second lines extend downwardly toward the first line.

4. The bag of claim 1 wherein the second lines extend laterally toward the first line.

5. The bag of claim 1 wherein the ends of the second lines are located intermediate the ends of the first line and the raised portion of the first line.

6. The bag of claim 1 wherein the ends of the second lines are located adjacent the ends of the first line.

7. The bag of claim 1 wherein the ends of the first line and second lines are located adjacent a lateral central portion of the flap.

8. The bag of claim 1 wherein the raised portion comprises a lateral central vertical line.

9. The bag of claim 1 wherein the joinder line comprises a pair of opposed third lines extending upwardly from edges of the flap beneath the second lines and having ends spaced from the ends of the first line.

10. The bag of claim 1 wherein the bag has five flaps located progressively along the backing sheet.

11. The bag of claim 1 including a pair of spaced openings adjacent an upper edge of the backing sheet.

* * * * *